(12) United States Patent
Anthony et al.

(10) Patent No.: US 10,010,509 B2
(45) Date of Patent: Jul. 3, 2018

(54) APPARATUS AND METHOD FOR PRODUCING CONTROLLED DOSAGE OF BIOACTIVE AGENT

(75) Inventors: Thomas Anthony, Sunnyvale, CA (US); Yaacov Almog, Nes Ziona (IL); Omer Gila, Cupertino, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 271 days.

(21) Appl. No.: 14/353,045

(22) PCT Filed: Oct. 28, 2011

(86) PCT No.: PCT/US2011/058244
§ 371 (c)(1),
(2), (4) Date: Apr. 21, 2014

(87) PCT Pub. No.: WO2013/062570
PCT Pub. Date: May 2, 2013

(65) Prior Publication Data
US 2014/0248416 A1    Sep. 4, 2014

(51) Int. Cl.
*A61K 9/48*    (2006.01)
*A61K 9/00*    (2006.01)
(Continued)

(52) U.S. Cl.
CPC ............. *A61K 9/4833* (2013.01); *A61J 3/078* (2013.01); *A61K 9/0056* (2013.01);
(Continued)

(58) Field of Classification Search
CPC .... B41J 2/01; B41J 2/04; C03C 17/00; B41M 5/00
(Continued)

(56) References Cited

U.S. PATENT DOCUMENTS 6,702,683 B2    3/2004  Abrams et al.
6,923,979 B2    8/2005  Fotland et al.
(Continued)

FOREIGN PATENT DOCUMENTS

CN    201793915 U    4/2011
EP    1306071        5/2003
(Continued)

OTHER PUBLICATIONS

McKeen, Fluorinated Coatings and Finishes Handbook: TheDefinitive User's Guide, 2006, Plastic Design Library, pp. 136 and 137.*
(Continued)

*Primary Examiner* — Dah-Wei D Yuan
*Assistant Examiner* — Andrew Bowman
(74) *Attorney, Agent, or Firm* — HP Inc. Patent Department

(57) ABSTRACT

An apparatus for producing a controlled dosage of bioactive agent is disclosed. The apparatus includes: a print device to eject a drop of a mixture onto an ingestible substrate, wherein the drop of mixture includes a bioactive agent within an ingestible carrier fluid and is between 50 ng and 1000 ng in size; a charge generating device adjacent to the print device to generate charge on the bioactive agent to draw the bioactive agent to the ingestible substrate; a cold fluid removal device adjacent to the charge generating device to remove a portion of the ingestible carrier fluid from the bioactive agent; an application device adjacent to the cold fluid removal device to apply an ingestible layer on top of the ingestible substrate encapsulating the bioactive agent or to fold the ingestible substrate on top of the bioactive agent encapsulating the bioactive agent; and a transfer device adjacent to the print device, the charge generating device, the cold fluid removal device, and the
(Continued)

application device to move the ingestible substrate from one device to the next.

20 Claims, 3 Drawing Sheets

(51) Int. Cl.
*A61K 9/70* (2006.01)
*A61J 3/07* (2006.01)
*B05D 1/02* (2006.01)
*B05D 1/06* (2006.01)
*B05C 11/02* (2006.01)
*B05C 9/12* (2006.01)
*B41J 2/385* (2006.01)

(52) U.S. Cl.
CPC .............. *A61K 9/7007* (2013.01); *B05C 9/12* (2013.01); *B05C 11/025* (2013.01); *B05D 1/02* (2013.01); *B05D 1/06* (2013.01); *B05D 2202/00* (2013.01); *B05D 2203/30* (2013.01); *B05D 2401/32* (2013.01); *B41J 2/3855* (2013.01)

(58) Field of Classification Search
USPC ................. 347/102, 54; 523/160; 428/32.18; 427/369
See application file for complete search history.

(56) References Cited

U.S. PATENT DOCUMENTS

| | | | |
|---|---|---|---|
| 7,052,124 B2* | 5/2006 | Pickup | B41J 11/002 347/101 |
| 7,819,847 B2 | 10/2010 | Vitello et al. | |
| 2003/0225188 A1* | 12/2003 | Horie | C09D 11/36 523/160 |
| 2004/0081689 A1 | 4/2004 | Dunfield et al. | |
| 2004/0137140 A1 | 7/2004 | Childers | |
| 2005/0233000 A1 | 10/2005 | Figueroa et al. | |
| 2010/0188464 A1* | 7/2010 | Peleg | B41J 2/2114 347/54 |
| 2011/0156315 A1 | 6/2011 | Khinast et al. | |
| 2012/0128902 A1* | 5/2012 | Panettieri | D21H 17/66 428/32.18 |

FOREIGN PATENT DOCUMENTS

| | | |
|---|---|---|
| WO | WO-2005-089713 | 9/2005 |
| WO | 2009134273 | 11/2009 |
| WO | WO-2011057164 | 5/2011 |

OTHER PUBLICATIONS

Hewlett-Packard Development Company, LP., International Search Report, dated May 16, 2012, Application No. PCT/US2011/058244, filed Oct. 28, 2011.

* cited by examiner

APPARATUS AND METHOD FOR PRODUCING CONTROLLED DOSAGE OF BIOACTIVE AGENT

BACKGROUND

Oral administration of pharmaceuticals is one of the most widely used methods for providing effective therapy for a variety of illnesses. For example, many powdered medications are administered orally to a person in dosage form such as tablets or capsules, while other medications are administered in liquid form.

Many individuals suffer from chronic health problems that require the regular administration of medicines, supplements, or other like substances. Diseases including, but not limited to, diabetes, allergies, epilepsy, heart problems, AIDS, and cancer all require the regular delivery of precise doses of medicine if patients are to survive over long periods of time. In some cases, some such medicines have a narrow therapeutic range and must be precisely dosed. If the patient falls below the range, the desired effect will not occur, and if the patient is above the range, then, the risk of toxic side effects increases. Additionally, in some cases, treatment plans require multiple medications that need to be taken all at once.

However, many pharmaceutical doses in tablet or capsule form are made in formulations of a predetermined amount of an active ingredient, such as 50 mg, 100 mg, etc. and/or a predetermined set of one or more active ingredients. Accordingly, it is often difficult or virtually impossible to split or divide a tablet or capsule to decrease or customize the dose administered. In fact, splitting or breaking of such tablets or capsules often results in fragments of unequal sizes. Therefore, researchers continue to seek improvements to pharmaceutical manufacturing processes such that variable doses of medicine and other pharmaceuticals can be easily formed.

BRIEF DESCRIPTION OF THE DRAWINGS

The detailed description will make reference to the following drawings, in which like reference numerals may correspond to similar, though perhaps not identical, components. For the sake of brevity, reference numerals having a previously described function may or may not be described in connection with other drawings in which they appear.

DETAILED DESCRIPTION

Figure 1:
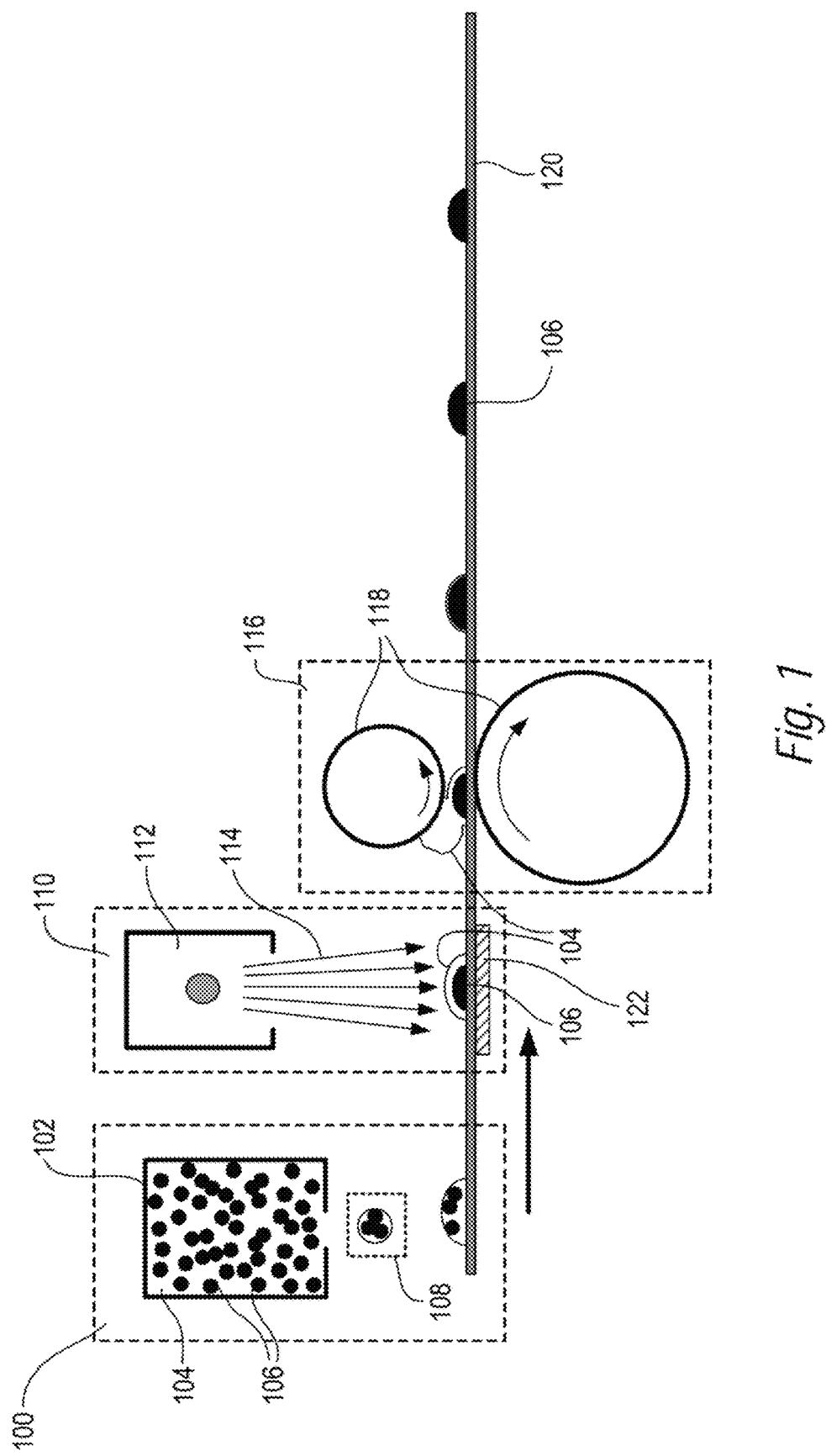
FIG. 1 depicts a schematic of a device to make a bioactive dose including a printer to jet controlled doses of bioactive agent onto an ingestible substrate, a device to draw or pin the bioactive agent onto the ingestible substrate, and a cold fluid removal device to remove excess carrier fluid, according to one example of principles described herein.

Reference is now made in detail to specific examples of the disclosed device to make a bioactive dose and specific examples of ways for making a bioactive dose. When applicable, alternative examples are also briefly described.

As used herein, the singular forms "a," "an," and "the" include plural referents unless the context clearly dictates otherwise.

As used in this specification and the appended claims, "approximately" and "about" mean a ±10% variance caused by, for example, variations in manufacturing processes.

As used herein, "bioactive agent" means a composition that affects a biological function of a vertebrate directly or as a result of a metabolic or chemical modification associated with the vertebrate or its vicinal environment. An example of a bioactive agent is a pharmaceutical substance, such as a drug, which is given to alter a physiological condition of the vertebrate, such as a disease. In other words, a bioactive agent is meant to include any type of drug, medication, medicament, vitamin, nutritional supplement, other compound or combination thereof that is designed to affect a biological function of a vertebrate.

As used herein, "cold" means any temperature at which the evaporation rate of the carrier fluid is insufficient to remove a majority of the liquid during manufacture of the bioactive dose.

As used herein, "inactive" shall mean not biologically active.

As used herein, "ingestible" means any composition that is suitable for human consumption and is non-toxic. Furthermore, as used herein, "suitable for human consumption" means any substance that complies with applicable standards, such as food, drug, and cosmetic regulations in the United States.

In the following detailed description, reference is made to the drawings accompanying this disclosure, which illustrate specific examples in which this disclosure may be practiced. The components of the examples can be positioned in a number of different orientations and any directional terminology used in relation to the orientation of the components is used for purposes of illustration and is in no way limiting. Directional terminology includes words such as "top," "bottom," "front," "back," "leading," "trailing," etc.

It is to be understood that other examples in which this disclosure may be practiced exist, and structural or logical changes may be made without departing from the scope of the present disclosure. Therefore, the following detailed description is not to be taken in a limiting sense. Instead, the scope of the present disclosure is defined by the appended claims.

Traditionally, pharmaceuticals and dietary supplements have been manufactured by mixing bioactive agents with secondary ingredients, and then mechanically pressing the mixture into the form of a tablet or encapsulating the powder version of the mixture in an ingestible capsule. Such batch processing may be inherently inflexible with respect to manufacturing of desired dosages of bioactive agents and requires costly cleaning of equipment when switching between products. Additionally, in some cases, patients may require more personalized treatment, resulting in, as discussed above, the prescription of tablets or ingestible capsules with more than one bioactive agent for treating one or more health conditions or the prescription of tablets or ingestible capsules containing non-standard amounts of bioactive agents.

Recently, researchers have proposed inkjet printing processes as a way of manufacturing pharmaceuticals (see, e.g., Brian Craig Lee, U.S. Pat. No. 6,962,175, Nov. 8, 2005 and Iddys D. Figueroa, U.S. Pat. No. 7,727,576, Jun. 1, 2010). In the case of jettable formulations of bioactive agents, up to 95 weight % (wt %) of the formulation may be inactive carrier fluid. Removal of this inactive carrier fluid prior to encapsulation of the bioactive agents in a capsule is critical in order to manufacture commercial pharmaceuticals. In the past, evaporation by heating, or thermal evaporation, has been proposed. However, bioactive agents are often temperature sensitive and may degrade in the presence of heat. Additionally, the energy required to evaporate the excess carrier fluid can be substantial, and the cost of extra equipment necessary to accommodate the longer web path required in order to accomplish evaporation may be high.

In one example illustrating the disadvantages of thermal evaporation, 1 milligram (mg) of a bioactive agent and 9 mg of water, acting as a carrier fluid, may be deposited onto 5 square centimeters ($cm^2$) of an ingestible substrate. In this example, the thickness of the jetted mixture is 18 µm and the areal density is 0.0018 $g/cm^2$. Evaporating this quantity of water may require about 4.1 $Joules/cm^2$, which translates to a power consumption of 4.1 kilowatts (kW) total, if the inkjet process has a substrate with a width of 20 cm and is at a print speed of 0.5 meters per second (m/s), about a quarter of the speed of a commercial high speed inkjet printer. Additionally, assuming that the time required to evaporate the 18 µm of water is limited by the diffusion of water vapor from a substrate at 50° C., the inkjet printing equipment may need to allow for 9 m of drying distance. Faster processing speeds may require proportionally more power and longer drying distances. Therefore, pharmaceutical manufacturing by inkjet printing processes with thermal evaporation may be unattractive because bioactive agents may be sensitive to heat and the necessary equipment may be expensive and may require high power consumption.

In accordance with the teachings herein, a device and corresponding method for manufacturing doses of bioactive agents by inkjet printing onto and in between ingestible sheets and removing excess inactive carrier fluid by cold fluid removal is presented. In this method, and as further discussed below, removal of the inactive carrier fluid by cold fluid removal may be accomplished by using a charge generating device to draw bioactive particles to a substrate and then using a contact roller or other cold fluid removal device to remove excess carrier fluid. Cold fluid removal may remove a sufficient amount of excess carrier fluid from the bioactive particles such that the remaining fluid may evaporate without the need for additional equipment. As a result, the upper surface of the ingestible substrate is left substantially free of liquid so that the bioactive agents may be readily encapsulated.

The device and corresponding method of manufacturing doses of bioactive agents utilizing the cold fluid removal approach disclosed herein has multiple advantages. First, in comparison to a method utilizing thermal evaporation, using cold removal of excess carrier fluid may use 30 times less drying power and may require 30 times less roller distance for drying. For example, the power necessary for removing about 10 µm thick of excess carrier fluid using the cold fluid removal process may be only a few watts, while the power necessary for completing the same process using thermal evaporation may be on the order of a kilowatt. Additionally, in this example, the roller space needed in the cold fluid removal process may be less than 0.5 m, whereas 5 to 10 m of roller space may be needed in a fluid removal process using thermal evaporation. Second, the cold fluid removal process may be inexpensive and the necessary equipment may be enabled to recycle carrier fluid with little additional production floor space resulting in cost savings. Third, the process does not subject the bioactive agents to elevated temperatures and therefore, there may be a decreased risk of degradation of the bioactive agents due to heat.

It should be noted that inkjet printing systems using cold fluid removal have been studied in the past (e.g. Omer Gila, U.S. Published Application 20110058001 Mar. 10, 2011). However, as further described below, the apparatus capable of producing controlled dosages of bioactive agents may include a printer capable of producing larger sized drops of bioactive agents; the apparatus disclosed herein may be capable of producing between 50 to 1000 ng sized drops whereas previous inkjet printing systems may be capable for producing between 3 to 15 ng sized drops.

FIG. 1 depicts one example of a device to make a bioactive dose including a printer to jet doses of a bioactive agent onto an ingestible substrate 100, a device to draw the bioactive agent to the ingestible substrate 110, and a cold fluid removal device to remove excess carrier fluid 116.

A suitable formulation including a bioactive agent 106 may be produced by mixing the bioactive agent 106 with an inactive carrier fluid 104. In one example, the bioactive agent 106 may be made in powder form using standard chemical manufacturing processes and then, introduced into the carrier fluid using high shear mixing, bead milling, ultrasonic agitation or microfluidization in order to create a particulate dispersion of bioactive agent in carrier fluid. In other examples, the bioactive agent may be dissolved in the carrier fluid or dissolved in a secondary liquid vehicle that is immiscible in the carrier fluid. In the example wherein a secondary liquid vehicle is used, an emulsion may be created when the secondary liquid vehicle (including the soluble bioactive agent) and a dispersing agent are added to the carrier fluid. In one such example, food-grade mineral oil may be used as the carrier liquid, and water may be used as a secondary vehicle. In some examples, dispersing agents such as lecithin may be added to stabilize the dispersion. Furthermore, in some examples, the bioactive agent 106 may be insoluble in the carrier fluid 104, and in other examples, as further discussed below, the bioactive agent 106 may be soluble in the carrier fluid 104 but may precipitate out of the solution when it makes contact with the substrate 120 it is jetted on.

In some examples, the bioactive agent particles 106 may be between 25 nanometers (nm) and 500 nm in diameter, and as described above, may be any material that alters a physiological condition of the vertebrate, such as a disease. In some examples, the bioactive agent may include more than one type of bioactive particle, such as, for example, a vitamin and a medicament or two types of medicaments.

In one example, the bioactive agent 106 may be mixed with a non-polar, food-grade liquid, such as PURETOL® mineral oil (Suncor Energy, Calgary, Alberta). In other examples, vegetable oils, such as safflower, sunflower, corn, soybean, canola, peanut or palm oils, other similar dielectric liquids, or a combination thereof may be used as a carrier liquid. As discussed below, in some examples wherein the device for drawing the bioactive agent 106 to the substrate 120 is a charge generating device, such non-polar, food-grade liquids may act as an inactive carrier fluid 104 during the electrical process that may be employed to charge the bioactive agent and then, draw such bioactive agent to an ingestible substrate. In such examples, a non-polar (dielectric) carrier fluid may enable electrical separation of bioactive agent particles from the carrier liquid. On the other hand, a conductive, highly polar carrier, such as water, may screen injected charge, which may prevent electrical separation of particles from a carrier. Furthermore, in some examples, as briefly discussed above, additional ingestible dispersants such as lecithin may further be mixed in to introduce either steric or charge stabilization of the bioactive agent particles.

Next, in some examples, the bioactive agent mixture 108 may be introduced into any printing device 102 including, but not limited to, suitable production digital jetting devices. In some examples, these apparatuses may contain an apparatus 100 for jetting the mixture of bioactive agent 108 to a substrate 120, an apparatus 110 for drawing or pinning the bioactive agent 106 to the ingestible substrate 120, and an apparatus 116 for removing excess carrier fluid 104 using cold fluid removal. In some examples, the substrate may move from the jetting apparatus 100 to the pinning apparatus 110 to the fluid removal apparatus on a belt, drum or any other mechanical device capable of moving the substrate 120.

The bioactive agent mixture 108 may be jetted onto a suitable ingestible substrate 120. The suitability of a substrate 120 may vary depending on the nature of the bioactive agent 106 but may, in general, be safely edible or ingestible. In some examples, the substrate 120 may dissolve or degrade in body fluids or enzymes. However, the substrate 120 may alternatively be made of non-degradable materials that may be readily eliminated by the body's natural processes. In some examples, the substrate 120 may be hydrophilic and may readily disintegrate in water, and in other examples, the dissolution or disintegration of the substrate 120 may be enhanced by the pH of the fluids in the stomach or upper intestine. In some examples, the materials of the substrate 120 may be chosen specifically to minimize unintended interactions with bioactive agents 106 when the bioactive agent mixture 108 is jetted onto the surface of the substrate. In some examples, other properties of the ingestible substrate 120 that may be desirable may include the ability to remain stable over extended periods of time at elevated temperatures or at high or low levels of relative humidity, being a poor medium for microorganism growth, or having reasonable mechanical properties. In some examples, the substrate 120 may have a tensile strength sufficient to allow it to be free-standing without need for any additional backing material.

In some examples, the substrate 120 may include one or more suitable, ingestible organic materials. In some examples, such suitable materials may be any material that does not adversely affect the mechanical integrity of the substrate as a free-standing web. Examples of such materials may include, but are not limited to, natural or chemically modified starch; glycerin; proteins such as gelatin or other similar compounds; cellulose derivatives such as hydroxypropylmethylcellulose or other similar compounds; polysaccharides such as pectin, xanthan gum, guar gum, algin or other similar compounds; synthetic polymers such as polyvinyl alcohol, polyvinylpyrrolidone or other similar compounds; or restructured fruits or vegetables such as milk proteins, rice paper, potato wafer sheets or other films made from restructured fruits or vegetables.

In some examples, the ingestible substrate 120 may further contain a water-expandable foam to aid in the rapid release of bioactive agents 106, such as oxidized regenerated cellulose commercially available from Johnson and Johnson under the trademark SURGICEL® (New Brunswick, N.J.) or a porcine derived gelatin powder commercially available from Pharmacia Corporation under the trademark GELFOAM® (New York, N.Y.). Additionally, in some examples, the ingestible substrate 1210 may further contain flavoring additives to make ingestion easier.

Regarding a suitable form for the ingestible substrate 120, in some examples, the substrate 120 may be in any form recognized in the printing industry such as paper, cardboard or polymeric films. In some examples, the ingestible substrate 120 may be uniform in thickness and in width. In some examples, the thickness of the ingestible substrate 120 may depend on the interactions between a particular substrate 120 and a desired bioactive agent 106 and the particular method of manufacture used. In some examples, the thickness of the ingestible substrate 120 may range from about 10 to about 350 microns.

The ingestible substrate 120 may be produced by a wide variety of methods including, but not limited to, roll coating, extruding, spray coating, and inkjetting. In some examples, a doctor blade may be employed to regulate the thickness of the deposited layer. In other examples, other similar devices may be used to regulate thickness. The ingestible substrate 120 may be a free-standing layer (i.e. without additional backing) or may be adhered to a sacrificial backing material. In examples wherein a sacrificial backing material is used, such backing material may serve multiple purposes. In some examples, such backing material may offer mechanical support to the ingestible substrate 120, may provide an electrically conductive surface which may serve as a ground plane during electrostatic pinning, or may serve as a medium on which information relevant to the consumer (e.g., medication name, dosage, manufacturing date, patient name, administration schedule, etc.) may be printed, as further discussed below. In some examples, the sacrificial backing material may be removed prior to packaging or may be included as a peel-off component that a user of the bioactive dose may remove prior to taking the bioactive dose.

While FIG. 1 depicts an example of a device in which the ingestible substrate is fed into the printing zone as a continuous web, alternatively, in other examples, the ingestible substrate may be deposited as a film onto a rotating drum by roll coating or any other suitable means, wherein the bioactive dose may formed by jetting of the bioactive dose 108 onto the substrate 120, electrical separation of bioactive agent 106, and cold removal of excess carrier liquid 104. In such an example wherein a rotating drum is used, the ingestible substrate 120 with doses of bioactive agent 108 is transferred from the drum onto another ingestible substrate similar to the ingestible substrate 120 disclosed here, resulting in doses of bioactive agent 106 encapsulated between two ingestible layers. The second ingestible layer may also be supported by a sacrificial backing material that may offer mechanical support or may contain printed information relevant to the consumer.

The printer for jetting the bioactive agent mixture 108 onto the ingestible substrate 120 may include any suitable components and as discussed previously, has been studied in the past. In some examples, an inkjet ink head may be used. In such an example, the inkjet head may be a piezo-electric inkjet head, a thermal inkjet head or any other type of inkjet head. In other examples, a spray or nozzle may be used. In some examples, the printer is capable of jetting a 50 nanogram (ng) to 1000 ng sized drop onto the substrate 120.

In some examples, the printer may further include a digital controller or other control device which may control the volume of bioactive agent mixture 108 jetted onto the substrate 120. Additionally, in some examples, the printer may further include a device for printing information onto the substrate 120, including information about the date of manufacture, information about the bioactive agent or other information. The information may be in any form for conveying information, such as text, characters or graphics.

In other examples, such a device may be a separate device from the printer and adjacent to the charge generator or the cold fluid removal device.

In some examples and as further described below in FIG. 2, after the bioactive agent mixture 108 is jetted onto the ingestible substrate 120, the bioactive agents 108 in the mixture 108 may be drawn to the substrate 120. In some examples, drawing of the bioactive agents 106 to the substrate 120 is accomplished using a device 112 that generates positive or negative charge, on the bioactive agents. In one example, a corona may be used. In other examples, a scorotron, ion head or any other suitable charge generating device may be used. In some examples, a ground plane 122 may be below the substrate 120 in order to provide a source of image charge, or a mirror amount of the opposite charge. In other examples, the ground plane 122 may be any conducting sacrificial backing material attached to the ingestible substrate 120; in yet other examples, it may be any conductive material adjacent to the substrate such that the substrate 120 is between the charge generating device 112 and the ground plane 122 consisting of the conductive material.

As seen in FIG. 1, in some examples, the inactive carrier fluid 104 may next be separated from the bioactive agent 106 using cold fluid removal. In one example, fluid may be removed by passing the substrate 120 with the mixture 108 on the surface of it between two contact rollers 118 that squeeze the carrier fluid 104 from the jetted mixture 108. In such an example, the contact rollers 118 may remove a sufficient amount of excess carrier fluid 104 from the bioactive particles 106 such that the remaining fluid may evaporate without need for additional equipment. In one example, the contact rollers 118 may be squeegee rollers. In other examples, a non-contact roller spinning against the process direction, such as a reverse roller, or an air knife may be used. In yet other examples, a combination including at least two of a contact roller, a reverse roller, and an air knife may be used, Additionally, in some examples, the inactive carrier fluid 104 removed using the cold fluid removal process may be collected and recycled as carrier fluid. This feature may permit the use of certain desired carrier fluids in the manufacturing of bioactive doses that may otherwise be prohibitively expensive.

Then, the bioactive agent 106 may be encapsulated in an ingestible layer. Such encapsulation may be accomplished in any suitable way. In one example, a second ingestible layer may be applied to the top of the substrate 120 and bioactive agent 106 by jetting such second ingestible layer from any inkjet printhead. Other suitable methods include using a lamination device, a pulsed spray nozzle or a roll coater to apply the second ingestible layer. In another example, the substrate 120 itself may be cut, folded, sealed or otherwise manipulated such that it encapsulates the bioactive agent.

In some examples, individual doses may be defined by cutting or perforating the web of encapsulated bioactive agents to desired sizes using any suitable devices and processes. In one example, individual doses may be defined by perforating the ingestible substrate in a manner similar to a roll of postage stamps, such that a dose can be easily detached from a roll of doses. In other examples, other suitable devices and processes may be used.

Finally, in some examples, the printer to jet doses of a bioactive agent onto an ingestible substrate 100, the device to draw the bioactive agent to the ingestible substrate 110, and the cold fluid removal device to remove excess carrier fluid 116 may be in series with like devices. In one example, the printer 100, the device to draw the bioactive agent to the ingestible substrate 110 and the cold fluid removal device 116 are together one set of devices that are in series with one or more additional sets of devices including at least one printer 100, one device to draw the bioactive agent to the ingestible substrate 110, and one cold fluid removal device 116 as described herein. In other examples, the apparatus may include one or more printers 100 in a row, one or more devices to draw the bioactive agent to the ingestible substrate 110 in a row, and one or more cold fluid removal devices 116 in a row.

Figure 2:
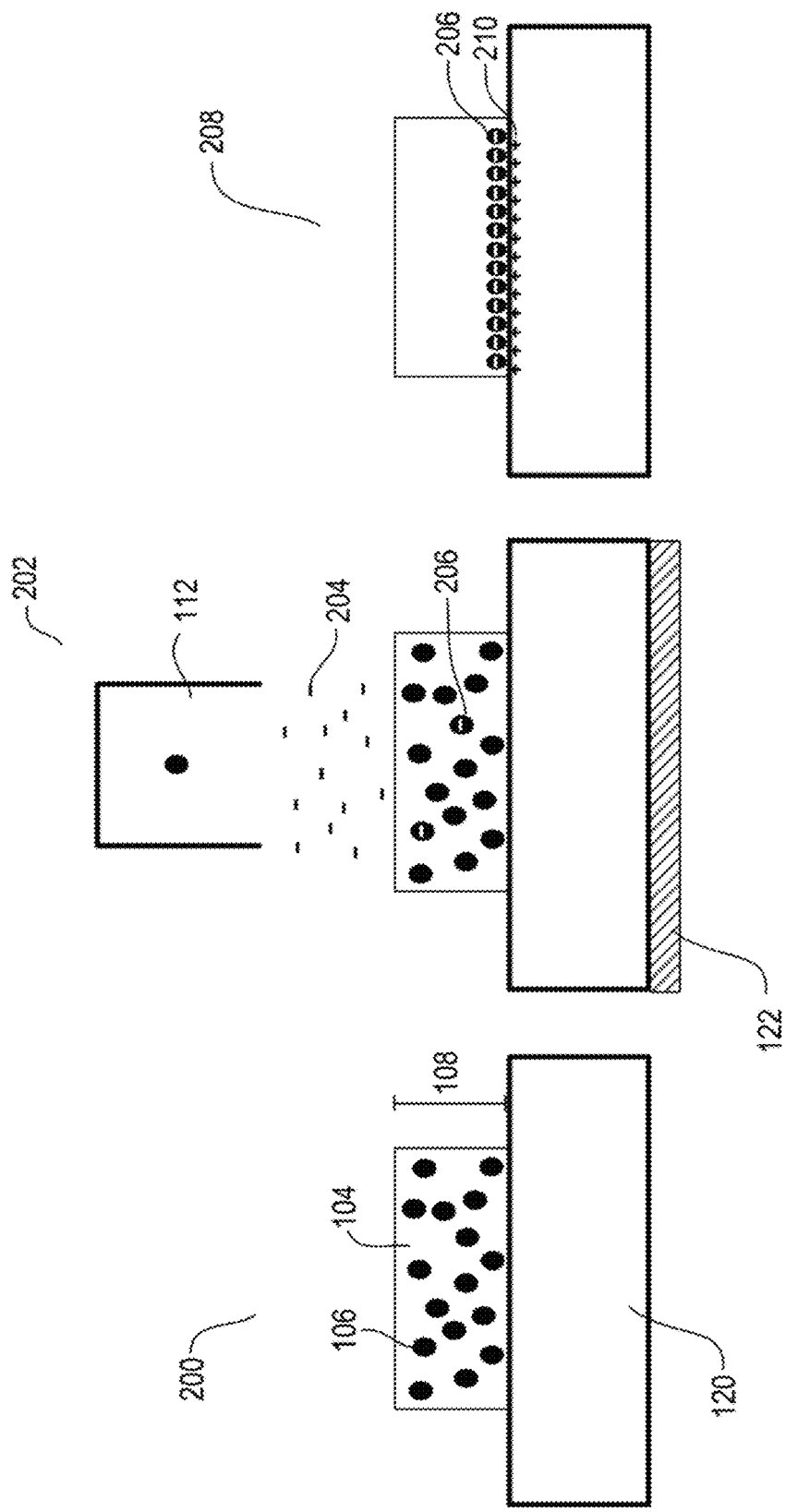
FIG. 2 depicts a schematic of a device to draw the bioactive agent to the ingestible substrate, according to one example of principles described herein.

FIG. 2 depicts one example of a device to draw the bioactive agent to the ingestible substrate including a device 112 to produce a charge.

As described above, after the bioactive agent mixture 108 is jetted onto the substrate 120, the bioactive agents 106 may be drawn to the substrate 120. In FIG. 2, one example of a device to draw the bioactive agent 106 to the substrate 120 using a corona 112 is shown. In such an example, the bioactive agents 106 may be exposed to a corona discharge (or an electrical discharge) of about 5 to 50 μA/cm of corona length. The discharge may be produced from a corona station with a power supply, such as an HV power supply. The power supply may be connected to a conductor, such as a small diameter wire or a series of needles. In this example, the airstream above the ingestible substrate 120 with the bioactive agent mixture 108 jetted onto it may become ionized, producing a stream of negative ions and electrons 204. These negative charges 204, drawn to the source of image charge as described above, may come into contact with the bioactive agents 106 and may be adsorbed onto the bioactive agent 106. The newly negatively charged bioactive agent 206 may then be drawn to the source for image charge 210 in a ground plane 122 adjacent to the substrate 120 and electrostatically "pinned" there. As described above, in some examples, the ground plane 122 may be a separate conductive material adjacent to the substrate such that the substrate is in between the charge generating device and the ground plane; in other examples, the ingestible substrate may be on top of a conducting sacrificial backing material that may provide a source of image charge. Additionally, in other examples, other charge generating devices capable of generating positive or negative charges may be used.

In some examples, additional interactions between the substrate 120 and the bioactive agents 206 may further bind or pin the bioactive agent 206 to the substrate 120. In other examples, as described above, other devices and processes may be used.

Figure 3:
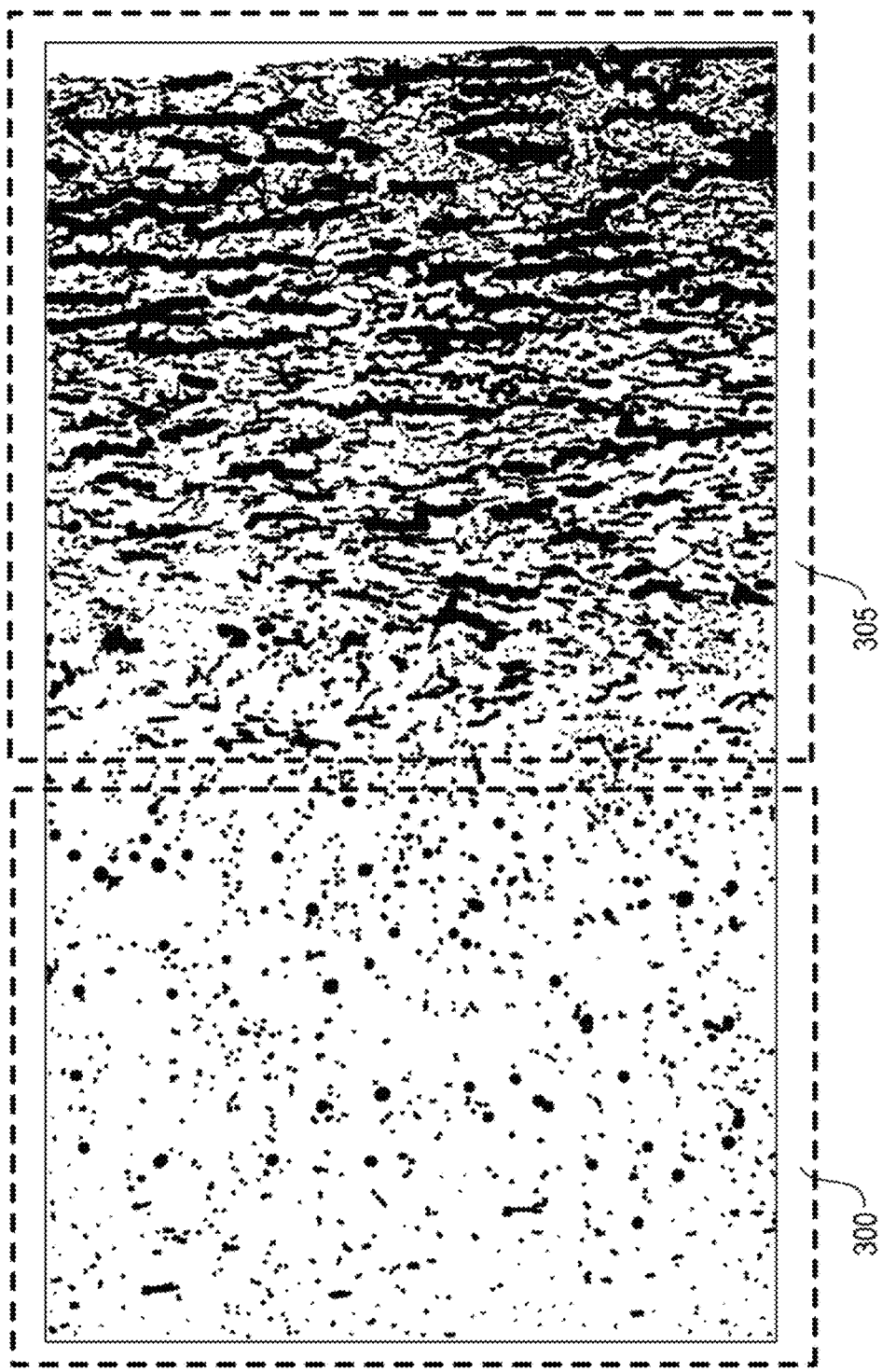
FIG. 3 is a depiction of bioactive agents sprayed onto a substrate, exposed and not exposed to a corona discharge, and then transferred to paper, according to one example of principles described herein.

FIG. 3 is an example depiction of a bioactive agent sprayed onto a substrate, exposed and not exposed to a corona discharge, and then transferred to paper. As seen in FIG. 3, drops of bioactive agents that have been exposed to a corona discharge or other like methods and drawn to the substrate resisted the shear force during transfer onto paper and remained pinned 300 (left side of Figure). On the other hand, drops of bioactive agents that were not drawn to the substrate smeared when being transferred onto paper 305 (right side of Figure). Accordingly, doses of bioactive agents may be more easily controlled and made uniform using the device and corresponding method for manufacturing pharmaceuticals disclosed herein.

What is claimed is:

1. An apparatus for making a controlled bioactive dose including:
    a container containing a mixture including a bioactive agent mixed with an ingestible carrier fluid;
    a print device to eject a drop of the mixture onto an ingestible substrate;

a charge generating device located above the ingestible substrate to charge the bioactive agent in the drop of the mixture after the drop of the mixture has landed on the ingestible substrate;

a conductive-material plate located below the ingestible substrate to draw the bioactive agent, charged by the charge generating device, towards the ingestible substrate to separate the ingestible carrier fluid from the bioactive agent;

a cold fluid removal device adjacent to the charge generating device to remove the ingestible carrier fluid from the bioactive agent after the ingestible carrier fluid is separated from the bioactive agent and before the bioactive agent is encapsulated;

an application device adjacent to the cold fluid removal device to apply an ingestible layer on top of the ingestible substrate to encapsulate the bioactive agent; and a transfer device to move the ingestible substrate from the print device to the charge generating device, to the cold fluid removal device, and to the application device.

2. The apparatus of claim 1 further including a control device connected to the print device to control the volume of the mixture ejected through the print device.

3. The apparatus of claim 1 wherein the ingestible carrier fluid is non polar; the substrate is organic and ingestible; and the bioactive agent includes a substance that affects a biological function of a vertebrate directly or as a result of a metabolic or chemical modification associated with the vertebrate or the vertebrate's vicinal environment and wherein the bioactive agent is between 25 nm and 500 nm in diameter.

4. The apparatus of claim 1 wherein the charge generating device corona particle separator, a scorotron or an ion head.

5. The apparatus of claim 1 wherein the cold fluid removal device includes two contact rollers.

6. The apparatus of claim 1 wherein the application device is one of an inkjet print head, a lamination device, a pulsed spray nozzle, and a roll coater.

7. The apparatus of claim 1 further including a second print device adjacent to the print device, the charge generating device, the cold fluid removal device, or the application device to print graphics, text, characters, symbols or a combination thereof onto the ingestible substrate.

8. The apparatus of claim 1 further including a cutting device or a perforating device adjacent to the application device to divide the encapsulated bioactive agent into a different size.

9. A method for manufacturing a controlled bioactive dose including:

ejecting, by a print device, a drop of mixture onto an ingestible substrate, wherein the drop of mixture includes a bioactive agent mixed with an ingestible carrier fluid;

charging, by a charge generating device located above the ingestible substrate, the bioactive agent in the drop of mixture after the drop of mixture has landed on the ingestible substrate;

separating the ingestible carrier fluid from the bioactive agent in the drop of mixture by having a conductive-material plate located below the ingestible substrate to draw the bioactive agent charged by the charge generating device towards the ingestible substrate;

after the ingestible carrier fluid is separated from the bioactive agent, removing the ingestible carrier fluid from the bioactive agent through a cold fluid removal device; and after the ingestible carrier fluid is removed from the bioactive agent, applying an ingestible layer on top of the ingestible substrate to encapsulate the bioactive agent.

10. The method of claim 9 further including controlling the volume of the ejected drop of mixture.

11. The method of claim 9 wherein the ingestible carrier fluid is non-polar and the bioactive agent includes a substance that affects a biological function of a vertebrate directly or as a result of a metabolic or chemical modification associated with the vertebrate or the vertebrate's vicinal environment.

12. The method of claim 9 wherein the step of removing the ingestible carrier fluid from the bioactive agent using cold fluid removal includes squeezing out the ingestible carrier fluid using a contact roller, a non-contact roller, an air knife or a combination thereof.

13. The method of claim 9 wherein the step of applying an ingestible layer on top of the ingestible substrate to encapsulate the bioactive agent includes jetting an ingestible layer on top of the ingestible substrate and the bioactive agent, laminating an ingestible layer on top of the ingestible substrate and the bioactive agent, roll coating an ingestible layer on top of the ingestible substrate and the bioactive agent, or perforating and folding the ingestible substrate on top of itself.

14. The method of claim 9 further including printing, by a second print device, graphics, text, characters, symbols or combinations thereof onto the ingestible substrate.

15. The method of claim 9 further including cutting or perforating the encapsulated bioactive agent into a different size.

16. An apparatus comprising:

a container containing a mixture including a bioactive agent mixed with an ingestible carrier fluid;

a print device to eject a drop of the mixture onto an ingestible substrate;

a charge generating device located above the ingestible substrate to charge the bioactive agent in the ejected drop of mixture on the ingestible substrate after the ejected drop of mixture has landed on the ingestible substrate;

a conductive-material plate located below the ingestible substrate to draw the bioactive agent in the drop of mixture, charged by the charge generating device, towards the ingestible substrate to separate the ingestible carrier fluid from the bioactive agent; and a cold fluid removal device adjacent to the charge generating device to remove a portion of the ingestible carrier fluid from the drop of mixture ejected on the ingestible substrate after the bioactive agent is drawn to separated from the ingestible substrate and before the bioactive agent is encapsulated.

17. The apparatus of claim 16, comprising:

an application device adjacent to the cold fluid removal device to apply an ingestible layer on top of the ingestible substrate encapsulating the bioactive agent or to fold the ingestible substrate on top of the bioactive agent encapsulating the bioactive agent.

18. The apparatus of claim 16, wherein the cold fluid removal device includes two contact rollers.

19. The apparatus of claim 16, comprising:

a source for image charge adjacent the ingestible substrate to positively charge the ingestible substrate, wherein the bioactive agent is negatively charged by the charge generating device, and the negatively charged bioactive agent is pinned to the positively charged ingestible substrate.

20. The apparatus of claim 1, comprising:

a source for image charge adjacent the ingestible substrate to positively charge the ingestible substrate, wherein the bioactive agent is negatively charged by the charge generating device, and the negatively charged bioactive agent is pinned to the positively charged ingestible substrate.

* * * * *

UNITED STATES PATENT AND TRADEMARK OFFICE
CERTIFICATE OF CORRECTION

PATENT NO. : 10,010,509 B2  
APPLICATION NO. : 14/353045  
DATED : July 3, 2018  
INVENTOR(S) : Thomas Anthony et al.

Page 1 of 1

It is certified that error appears in the above-identified patent and that said Letters Patent is hereby corrected as shown below:

In Column 9, Line 34, Claim 4, after "device" insert -- is a --.

In Column 10, Line 53, Claim 16, after "agent is" delete "drawn to".

Signed and Sealed this
Eleventh Day of December, 2018

Andrei Iancu
*Director of the United States Patent and Trademark Office*